United States Patent
Wang et al.

(10) Patent No.: US 9,429,544 B2
(45) Date of Patent: Aug. 30, 2016

(54) GMR BIOSENSOR WITH ENHANCED SENSITIVITY

(75) Inventors: Po-Kang Wang, San Jose, CA (US);
Xizeng Shi, Fremont, CA (US);
Chyu-Jiuh Torng, Fremont, CA (US)

(73) Assignee: Headway Technologies, Inc., Milpitas, CA (US)

( * ) Notice: Subject to any disclaimer, the term of this patent is extended or adjusted under 35 U.S.C. 154(b) by 0 days.

(21) Appl. No.: 13/417,399

(22) Filed: Mar. 12, 2012

(65) Prior Publication Data

US 2012/0169332 A1 Jul. 5, 2012

Related U.S. Application Data

(62) Division of application No. 11/497,162, filed on Aug. 1, 2006, now Pat. No. 8,133,439.

(51) Int. Cl.
*G01R 33/02* (2006.01)
*G01N 27/72* (2006.01)
(Continued)

(52) U.S. Cl.
CPC ............. *G01N 27/745* (2013.01); *B82Y 25/00* (2013.01); *G01R 33/05* (2013.01); *G01R 33/093* (2013.01);
(Continued)

(58) Field of Classification Search
CPC .... B82Y 25/00; B82Y 40/00; G01R 33/093; G01R 15/205; G01N 15/0656; H01F 41/302
USPC ...... 422/50, 68.1, 82.02; 324/219, 232, 252, 324/262, 301
See application file for complete search history.

(56) References Cited

U.S. PATENT DOCUMENTS 5,981,297 A 11/1999 Baselt
6,437,563 B1 8/2002 Simmonds et al.
(Continued)

FOREIGN PATENT DOCUMENTS

EP 1 666 894 6/2006
WO WO 03/054566 7/2003
(Continued)

OTHER PUBLICATIONS

"A biosensor based on magnetoresistance technology," by David R. Baselt et al., Biosensors & Bioelectronics 13, 731-739 (1998), found: http://stm2.nrl.navy.mil/1998bios/1998bios.html, on Aug. 23, 2006, pp. 1-12.
(Continued)

*Primary Examiner* — Dean Kwak
(74) *Attorney, Agent, or Firm* — Saile Ackerman LLC; Stephen B. Ackerman

(57) ABSTRACT

A sensor array comprising a series connection of parallel GMR sensor stripes provides a sensitive mechanism for detecting the presence of magnetized particles bonded to biological molecules that are affixed to a substrate. The adverse effect of hysteresis on the maintenance of a stable bias point for the magnetic moment of the sensor free layer is eliminated by a combination of biasing the sensor along its longitudinal direction rather than the usual transverse direction and by using the overcoat stress and magnetostriction of magnetic layers to create a compensatory transverse magnetic anisotropy. By making the spaces between the stripes narrower than the dimension of the magnetized particle and by making the width of the stripes equal to the dimension of the particle, the sensitivity of the sensor array is enhanced.

4 Claims, 3 Drawing Sheets

(51) Int. Cl.
  *G01N 27/74* (2006.01)
  *B82Y 25/00* (2011.01)
  *G01R 33/09* (2006.01)
  *G01R 33/05* (2006.01)
  *G01N 15/06* (2006.01)

(52) U.S. Cl.
  CPC ......... *G01R 33/098* (2013.01); *G01N 15/0656* (2013.01); *Y10T 29/49124* (2015.01); *Y10T 29/49986* (2015.01)

(56) References Cited

U.S. PATENT DOCUMENTS

| | | | |
|---|---|---|---|
| 6,504,363 B1 | 1/2003 | Dogaru et al. | |
| 6,518,747 B2 | 2/2003 | Sager et al. | |
| 6,775,109 B2 | 8/2004 | Gambino et al. | |
| 6,844,202 B2 | 1/2005 | Prinz et al. | |
| 6,875,621 B2 | 4/2005 | Tondra | |
| 6,995,557 B2* | 2/2006 | Goldfine et al. | 324/232 |
| 7,048,890 B2 | 5/2006 | Coehoorn et al. | |
| 7,282,755 B2 | 10/2007 | Pakala et al. | |
| 7,394,626 B2 | 7/2008 | Fukumoto et al. | |
| 2002/0060565 A1 | 5/2002 | Tondra | |
| 2002/0158626 A1* | 10/2002 | Shay et al. | 324/207.16 |
| 2004/0120185 A1* | 6/2004 | Kang et al. | 365/158 |
| 2004/0130323 A1* | 7/2004 | Oohashi et al. | 324/252 |
| 2005/0054120 A1* | 3/2005 | Wakui et al. | 438/3 |
| 2005/0087000 A1 | 4/2005 | Coehoorn et al. | |
| 2008/0169807 A1* | 7/2008 | Naito et al. | 324/252 |

FOREIGN PATENT DOCUMENTS

| | | |
|---|---|---|
| WO | WO 2006/018811 | 2/2006 |
| WO | WO 2006/047840 | 5/2006 |

OTHER PUBLICATIONS

"Design and performance of GMR sensors for the detection of magnetic microbeads in biosensors," by J.C. Rife et al., Sensors and Actuators A 107 (2003) 209-218, Elsevier.

"Giant magnetoimpedance and stress-impedance effects in multilayered FeSiB/Cu/FeSiB films with a meander structure," by Xin Hui Mao et al., XP002507805, J. Mater. Res. , vol. 18, No. 4, Apr. 2003, pp. 868-871.

European Search Report 11 006 801.2-1560 Mailed: May 21, 2013, MagIC Technologies, Inc.

Japanese Office Action 2013-054767 Mailed: Aug. 12, 2014, Headway Technologies Inc.

European Search Report 11 006 801.2 Mailed: Jun. 26, 2014, Headway Technologies Inc.

* cited by examiner

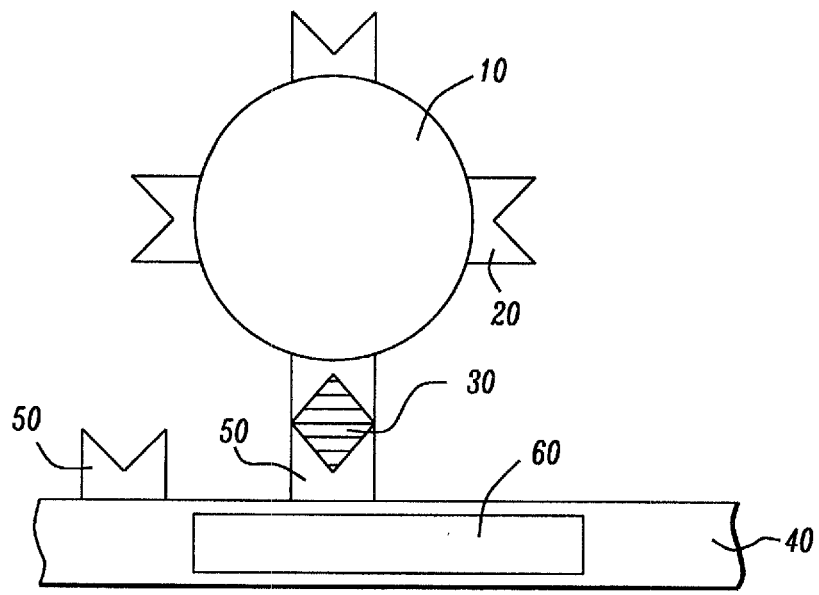
FIG. 1 — Prior Art
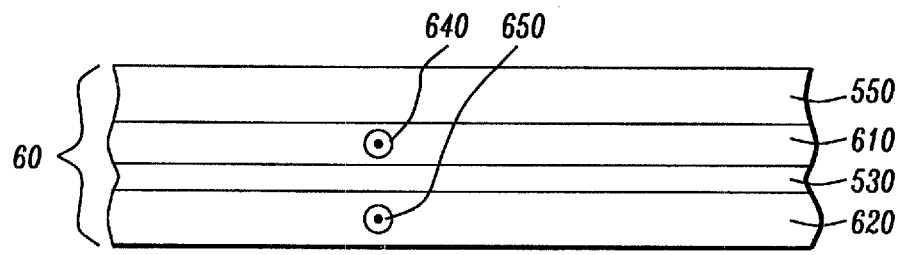
FIG. 2a — Prior Art
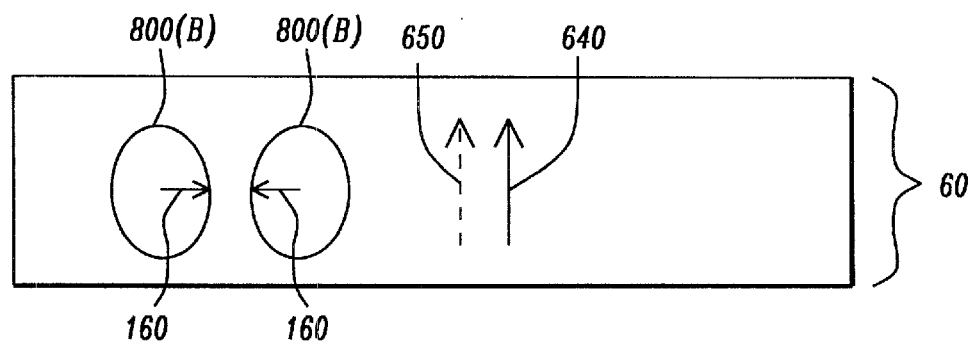
FIG. 2b — Prior Art

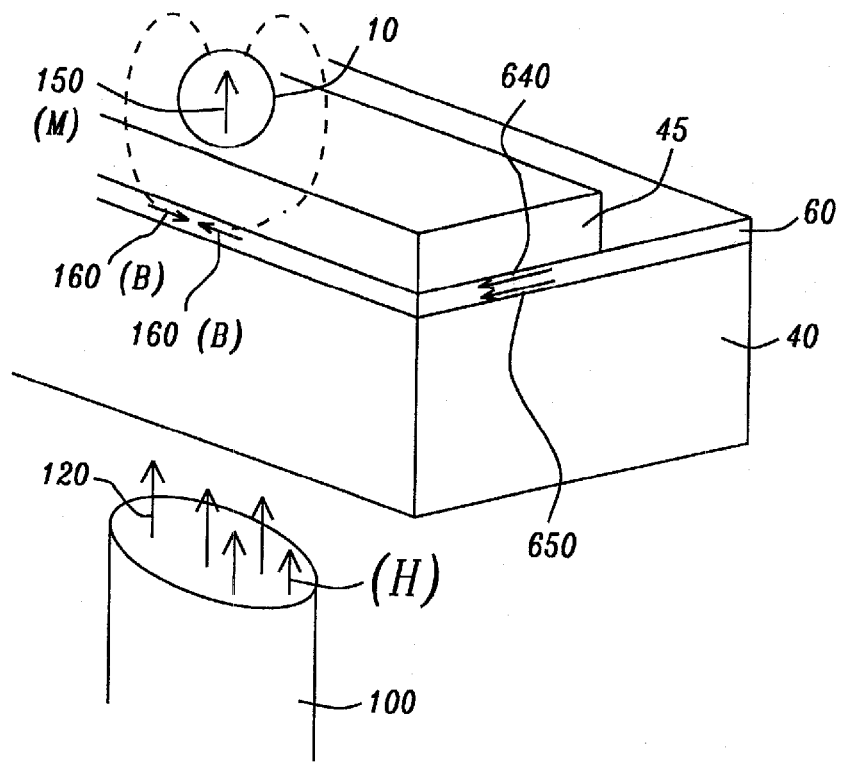
FIG. 3 - Prior Art
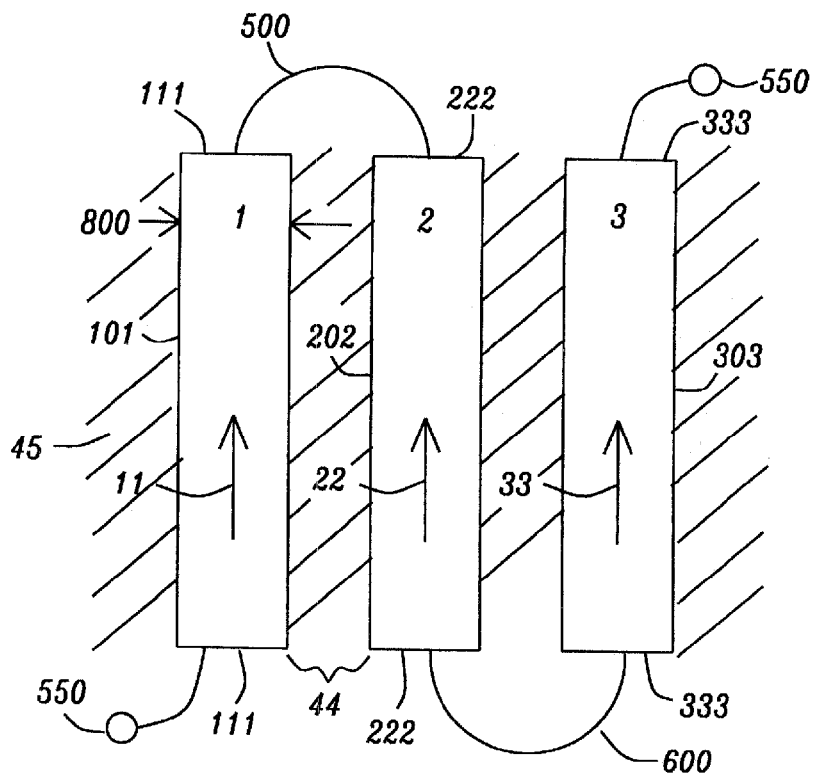
FIG. 4a

GMR BIOSENSOR WITH ENHANCED SENSITIVITY

This is a Divisional Application of U.S. patent application Ser. No. 11/497,162, filed on Aug. 1, 2006, which is herein incorporated by reference in its entirety and assigned to a common assignee.

BACKGROUND OF THE INVENTION

1. Field of the Invention

This invention relates to the detection of small magnetized particles (beads) by a GMR sensor, particularly when such particles or beads are attached to molecules whose presence or absence is to be determined in a chemical or biological assay.

2. Description of the Related Art

GMR (giant magnetoresistive) devices have been proposed as effective sensors to detect the presence of specific chemical and biological molecules (the "target molecules") when, for example, such target molecules are a part of a fluid mixture that includes other molecules whose detection is not necessarily of interest. The basic method underlying such magnetic detection of molecules first requires the attachment of small magnetic (or magnetizable) particles (also denoted "beads") to all the molecules in the mixture that contains the target molecules. The magnetic beads are made to attach to the molecules by coating the beads with a chemical or biological species that binds to the molecules in the mixture. Then, a surface (i.e., a solid substrate) is provided on which there has been affixed receptor sites (specific molecules) to which only the target molecules will bond. After the mixture has been in contact with the surface so that the target molecules have bonded, the surface can be flushed in some manner to remove all unbonded molecules. Because the bonded target molecules (as well as others that have been flushed away) are equipped with the attached magnetic beads, it is only necessary to detect the magnetic beads to be able, at the same time, to assess the number of captured target molecules. Thus, the magnetic beads are simply "flags," which can be easily detected (and counted) once the target molecules have been captured by chemical bonding to the receptor sites on the surface. The issue, then, is to provide an effective method of detecting the small magnetic beads, since the detection of the beads is tantamount to detection of the target molecules.

One prior art method of detecting small magnetic beads affixed to molecules bonded to receptor sites is to position a GMR device beneath them; for example, to position it beneath the substrate surface on which the receptor sites have been placed.

FIG. 1 is a highly schematic diagram (typical of the prior art methodology) showing a magnetic bead (10) covered with receptor sites (20) that are specific to bonding with a target molecule (30) (shown shaded) which has already bonded to one of the sites. A substrate (40) is covered with receptor sites (50) that are also specific to target molecule (30) and those sites may, in general, be different from the sites that bond the magnetic particle to the molecule. The target molecule (30) is shown bonded to one of the receptor sites (50) on the surface.

A prior art GMR sensor (60), shown without any detail, is positioned beneath the receptor site. As shown schematically in the cross-sectional view of FIG. 2a, the prior art GMR sensor ((60) in FIG. 1) (60), is preferably in the form of a laminated thin film stripe that includes a magnetically free layer (610) and a magnetically pinned layer (620) separated by a thin, non-magnetic but electrically conducting layer (530). Typically, the sensor will also include a capping layer or overlayer (550). The GMR properties of such a film stripe causes it to act essentially as a resistor whose resistance depends on the relative orientation of the magnetic moments of the free and pinned layers (shown here as arrows (640), (650) both directed out of the figure plane). FIG. 2b shows, schematically, an overhead view of the sensor of FIG. 2a, showing more clearly the direction of the magnetic moments (640) and (650), shown dashed, as it is below (640). Also shown are two lobes outlining a region of equal strength of an external magnetic field B (800). The field strength is shown directionally as arrows (160) that would be produced by a magnetized particle (not shown here) that is positioned above the sensor, as shown in FIG. 1. This will also be shown more clearly in FIG. 3, below. The field of the lobes will deflect (640) (deflection not shown), but leave (650) unchanged.

FIG. 3 shows, schematically, a magnetic particle (10) situated (by binding) over a surface layer (45) formed on a substrate (40) in a typical prior art configuration. The surface layer is required to support the bonding sites and can be a layer of $Si_3N_4$ and the substrate can be a Si substrate on or within which the required circuitry can be formed. For simplicity, a target molecule is not shown. A GMR sensor (60), as illustrated in any of the previous figures, is positioned between the surface layer and the substrate (40). An electromagnet (100) is positioned beneath the substrate and creates a magnetic field H (120) directed vertically through the substrate, the GMR sensor, and the magnetic bead. The external field, H, is directed perpendicularly to the magnetic moments of the GMR sensor (640), (650) so as not to change their relative orientations. Because of the magnetic properties of the bead, the external field H (120), induces a magnetic moment M (150), shown as an arrow in the bead which, in turn, produces a magnetic field B (160) that extends beyond the boundary of the bead as shown by the dashed lobes. The magnetic field B (160), in turn, penetrates the plane of the sensor and its component in that plane (shown as the lobes (800) in FIG. 2b) can change the orientation of the magnetic moment of the sensor free layer as is shown schematically in FIGS. 4a and 4b.

The magnetization of the free layer (640), is now changed in direction relative to the magnetization of the pinned layer (650), because of the presence of the magnetic field of the magnetized bead (160) that is directed within the plane of the free layer. Because the presence of the magnetized bead affects the magnetic moment of the free layer, it thereby, changes the resistance of the GMR sensor strip. By detecting the changes in resistance, the presence or absence of a magnetized bead is made known and, consequently, the binding of a target molecule is detected. Ultimately, an array of sensors can be formed beneath a substrate of large area that is covered by a large number of binding sites. The variation of the resistance of the sensor array is then a good indication of the number of target molecules that has been captured at sites and that number, in turn, can be related to the density of such target molecules in the mixture being assayed.

As is well known by those skilled in the field, although the magnetization of the free layer moves in response to external magnetic stimuli during operation of the sensor, the magnetization of the free layer is preferably fixed when the sensor is in a quiescent mode and not acted on by external fields. The fixing of the free layer magnetization under these conditions is called "biasing" the free layer and the position of the magnetic moment of the free layer in this position is called its bias point. It is also known to those skilled in the art that the bias position of the free layer is subject to the effects of hysteresis, which means that the bias position is not maintained after the magnetization of the free layer is made to cycle through positive and negative directions by external magnetic stimuli and a quiescent state is once again achieved. This hysteresis has a negative impact on the reproducibility of sensor readings, particularly when the external stimuli moving the free layer magnetization are small to begin with. One of the objects of the present invention will be to eliminate the adverse effects of hysteresis. Given the increasing interest in the identification of biological molecules it is to be expected that there is a significant amount of prior art directed at the use of GMR sensors (and other magnetic sensors) to provide this identification. A detailed research paper that presents an overview of several different approaches as well as the use of GMR sensors is: "Design and performance of GMR sensors for the detection of magnetic microbeads in biosensors" J. C. Rife et al., Sensors and Actuators A 107 (2003) 209-218. An early disclosure of the use of magnetic labels to detect target molecules is to be found in Baselt (U.S. Pat. No. 5,981,297). Baselt describes a system for binding target molecules to recognition agents that are themselves covalently bound to the surface of a magnetic field sensor. The target molecules, as well as non-target molecules, are covalently bound to magnetizable particles. The magnetizable particles are preferably superparamagnetic iron-oxide impregnated polymer beads and the sensor is a magnetoresistive material. The detector can indicate the presence or absence of a target molecule while molecules that do not bind to the recognition agents (non-target molecules) are removed from the system by the application of a magnetic field.

A particularly detailed discussion of the detection scheme of the method is provided by Tondra (U.S. Pat. No. 6,875,621). Tondra teaches a ferromagnetic thin-film based GMR magnetic field sensor for detecting the presence of selected molecular species. Tondra also teaches methods for enhancing the sensitivity of GMR sensor arrays that include the use of bridge circuits and series connections of multiple sensor stripes. Tondra teaches the use of paramagnetic beads that have very little intrinsic magnetic field and are magnetized by an external source after the target molecules have been captured.

Coehoorn et al. (US Pub. Pat. Appl. 2005/0087000) teaches a system that is similar to that of Tondra (above), in which magnetic nanoparticles are bound to target molecules and wherein the width and length dimensions of the magnetic sensor elements are a factor of 100 or more larger than the magnetic nanoparticles.

Prinz et al. (U.S. Pat. No. 6,844,202) teaches the use of a magnetic sensing element in which a planar layer of electrically conducting ferromagnetic material has an initial state in which the material has a circular magnetic moment. In other respects, the sensor of Prinz fulfills the basic steps of binding at its surface with target molecules that are part of a fluid test medium. Unlike the GMR devices disclosed by Tondra and Coehoorn above, the sensor of Prinz changes its magnetic moment from circular to radial under the influence of the fringing fields produced by the magnetized particles on the bound target molecules.

Gambino et al. (U.S. Pat. No. 6,775,109) teaches a magnetic field sensor that incorporates a plurality of magnetic stripes spaced apart on the surface of a substrate in a configuration wherein the stray magnetic fields at the ends of the stripes are magnetostatically coupled and the stripes are magnetized in alternating directions.

Simmonds et al. (U.S. Pat. No. 6,437,563) teaches a method of detecting magnetic particles by causing the magnetic fields of the particles to oscillate and then detecting the presence of the oscillating fields by inductively coupling them to coils. Thus, the sensor is not a GMR sensor as described above, but, nevertheless, is able to detect the presence of small magnetic particles.

Finally, Sager et al. (U.S. Pat. No. 6,518,747) teaches the detection of magnetized particles by using Hall effect sensors.

The methods cited above that rely on the use of a GMR sensor, rather than methods such as inductive sensing or Hall effect sensing, will all be adversely affected by the failure of the GMR sensor to maintain a reproducible bias direction for its free layer magnetization. This lack of reproducibility is a result of magnetic hysteresis that occurs whenever the external magnetic fields being detected cause the magnetic moment of the sensor free layer to cycle about its bias direction. In the present use of the GMR sensor to detect the presence of extremely small magnetized particles, the external fields are small. Because of this, methods to fix the bias point of the sensor free layer cannot fix it too strongly as this would limit the ability of the free layer magnetic moment to respond to the very stimuli it is attempting to measure. It is, therefore, necessary to find a way of fixing the free layer bias point while still allowing the magnetic moment sufficient freedom of motion to detect even very small external magnetic fields.

SUMMARY OF THE INVENTION

A first object of this invention is to provide a method of determining the presence or absence of small magnetized particles.

A second object of this invention is to provide such a method that detects the aforementioned magnetized particles when they are bonded to chemical or biological molecules.

A third object of the present invention is to provide such a method that uses the magnetoresistive properties of a GMR sensor to detect the presence of a small magnetized particle.

A fourth object of the present invention is to provide a GMR sensor to be used in detecting the presence of small magnetized particles wherein the response of the sensor to external magnetic fields is not adversely affected by a non-reproducibility of its free layer bias point due to magnetic hysteresis.

A fifth object of the present invention is to provide a GMR sensor having a high sensitivity and a free layer bias point that is reproducible.

The objects of the present invention will be achieved by a GMR sensor design having the following characteristics, all of which are schematically illustrated in FIGS. 4a and 4b and will be discussed below in greater detail.

1. The sensor consists of multiple long stripes (only three being shown here) of GMR films (1, 2, 3), electrically connected (500, 600) in series.

2. The free and pinned layers of each sensor stripe are magnetically biased, the biased magnetic moments being shown as single arrows, (11, 22, 33), in the lengthwise direction.

3. The sensor stripes are arranged in a serpentine configuration so that adjacent stripes are substantially parallel to each other and have the bias positions of their magnetic moments oriented in parallel directions.

4. The spacing (44) between neighboring sensor stripes is much smaller than the dimensions of the magnetic particles that they will be detecting.

5. The width of each stripe (800) is comparable to the dimensions of the magnetic particles being detected.

6. The structure of each individual stripe is a capped lamination (see FIG. 4*b*) comprising a free layer (99) and a pinned layer (77) separated by a metallic spacer layer (88), wherein the pinned layer can be a synthetic layer for enhanced pinning strength. The stripes are surrounded by insulating layers (45).

7. The magnetic anisotropy of each stripe is reduced by minimizing its free layer thickness and providing a minimal interlayer coupling between the free and pinned layers.

8. The free layer thickness is minimized, while not degrading the stripe's dR/R.

9. The interlayer coupling is minimized by adjusting the thickness of the metallic layer separating the free and pinned layers.

10. The film magnetostriction can be adjusted, in conjunction with an overcoat stress, to produce a net stress-induced anisotropy. With proper combination of these two stress factors, the easy axis of the stress-induced anisotropy can be oriented perpendicular to the longitudinal direction of the stripe, so as to cancel out the free layer shape anisotropy.

The characteristics enumerated above will produce a sensor having a reproducible bias point while still retaining a free layer magnetization that is responsive to the effects of small external magnetic fields. In particular, by orienting the bias direction along the lengthwise direction of the sensor stripe, the adverse hysteresis effects on a stable bias point will be offset by the shape anisotropy produced by a stripe shape that is longer than it is wide. By a combination of magnetostriction and stress-induced anisotropy that is perpendicular to the shape anisotropy, however, the overall magnetization remains responsive and the sensor is sensitive to small external fields. In addition, by forming a narrow space (less than bead diameter) between adjacent stripes in an array, making the width of the stripes comparable to the dimensions of the bead and by orienting adjacent sensor stripes parallel to each other, the position of a magnetic particle is likely to overlap two adjacent stripes, thereby, having its detectability enhanced by the series response of two stripes.

BRIEF DESCRIPTION OF THE DRAWINGS

The objects, features, and advantages of the present invention are understood within the context of the Description of the Preferred Embodiment as set forth below. The Description of the Preferred Embodiment is understood within the context of the accompanying figures, wherein:

FIG. 1 (prior art) is a schematic representation of a magnetic bead bonded to a target molecule and the target molecule bonded to a receptor site.

FIG. 2*a* (prior art) is a schematic cross-sectional representation of a GMR sensor such as is positioned beneath the substrate of FIG. 1.

FIG. 2*b* (prior art) is a schematic illustration of an overhead view of the sensor of FIG. 2*a*, showing also the presence of an external field produced by a magnetized particle.

FIG. 3 (prior art) is a schematic perspective representation of a typical biased GMR sensor stripe over which a magnetized particle is positioned.

FIG. 4*a* is a schematic overhead view of a sensor array formed of the sensor stripes of the present invention.

DESCRIPTION OF THE PREFERRED EMBODIMENTS

Figure 4B:
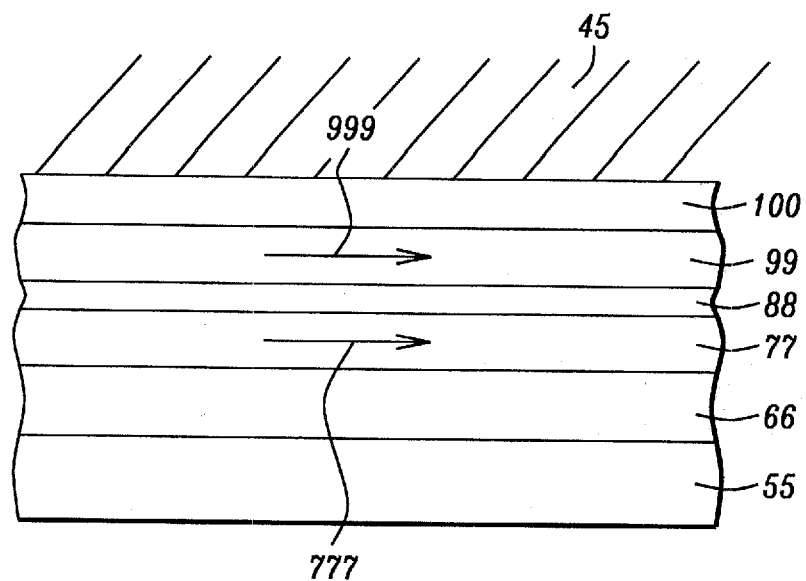
FIG. 4*b* is a cross-sectional schematic view of one sensor stripe of the array.

The preferred embodiments of the present invention are a GMR sensor stripe and an array of such GMR sensor stripes, capable of detecting the presence of magnetic particles or beads, typically bonded to chemical molecules. The GMR stripe and the array of stripes, by virtue of their formation, are not adversely affected by instability of a free layer bias point due to hysteresis. We use the term "stripe" to characterize a GMR sensor element and to emphasize the fact that it is deposited in the shape of a long, approximately rectangular strip or stripe. When used to detect magnetic particles bonded to target molecules (eg. in a bio-chemical assay) the array is formed beneath a surface on which are affixed bonding sites for target molecules. To perform the detection process, the target molecules whose presence is to be detected, as well as others that are not targets, are first magnetically tagged, by being bonded to small magnetic particles or beads that are subsequently magnetized by an external magnetic field.

The advantages of the present invention reside in the fact that the bias point of the free and pinned layer magnetizations of each GMR sensor stripe in the array is oriented along the lengthwise direction of the stripe. The fact that the stripes are thin and longer then they are wide, provides a shape anisotropy that maintains a bias point in the lengthwise direction that is stable with respect to hysteresis effects produced by the cyclic motion of the free layer magnetic moment during its use in detection processes. In order to ensure that the shape anisotropy does not adversely affect the sensitivity of the sensor to small external fields that move the magnetization away from the longitudinal bias direction, a compensating anisotropy is produced by combining a stress induced anisotropy due to magnetostriction of the sensor magnetic layers with the stresses in the magnetic layers produced by tension or compression of the various surrounding sensor overlayers that encapsulate the sensor. This combination of magnetostriction and compressional or tensile overlayer stress can be adjusted to reduce the overall magnetic anisotropy. Finally, the sensor free layer is made as thin as possible while not sacrificing the GMR ratio, dR/R, and the interlayer coupling between the free and pinned layers is adjusted to be smaller than the magnetic anisotropies.

The sensor stripes produced by the methods of this invention are then connected in electrical series in a serpentine fashion that places individual stripes side-by-side in a parallel configuration, with a narrow space between adjacent stripes and with the bias directions of their magnetizations (i.e., their magnetic moments) parallel. To achieve this configuration, the individual stripes are placed side-by-side as desired and then electrically connected between the aligned top and bottom edges of adjacent stripes with a conducting element to create a continuous electrical circuit. Because the stripes are very narrowly spaced (less than a bead diameter) and are very narrow themselves (approximately a bead diameter) there is a great likelihood that individual beads located above the stripes will straddle two adjacent stripes, thereby, enhancing the response of the array.

Because the methods of forming the binding surface, the nature and formation method of the binding sites and the means of attaching the magnetic beads to the target molecules are all well known in the art (see the above cited journal article and the prior art patents), the detailed description of the invention that now follows will be restricted to the construction of the sensor stripes and the array configuration.

Referring now to FIG. 4a, there is shown a schematic overhead view of a small array of GMR stripes or, equivalently, what could be a segment of a larger array, in which there are three electrically connected GMR sensor stripes of the present invention, denoted for reference purposes as stripes 1, 2 and 3. These stripes are of generally rectangular shape, having parallel lateral edges (101), (202), (303) of length between approximately 10 microns and 200 microns and parallel transverse edges (111), (222), (333) of width between approximately 1 micron and 5 microns. The stripes are connected in electrical series in an electrically conductive continuous serpentine configuration that aligns successive stripes adjacent to each other with their magnetic moments, when in a quiescent state, oriented in parallel (arrows (11), (22), (33)). The separation (44) between adjacent stripes (filled by the surrounding layers of insulation (45)) is less than the diameter of the magnetic particles to be detected, which are typically between approximately 0.2 microns and 1 micron. As can be seen in the figure, the co-linear upper transverse edges (111), (222) of stripes 1 and 2, are electrically connected with a conducting element (500), as are the lower transverse edges (222), (333) of stripes 2 and 3 (600). The free lower edge of stripe 1 (111) and the free upper edge of stripe 3 (333) are each conductively connected to terminal connectors (550) for the purpose of engaging the array within an external circuit (not shown). If the three stripes are part of a larger array, the terminal connectors would be absent and connections to other GMR stripes would be made. As can be envisioned, if the array consisted of M stripes, the connections would proceed, pairwise, in like fashion, with end stripes 1 and M being connected to terminals. It is understood that the array of FIG. 4a will be encapsulated within surrounding layers of insulation (45).

The dimensional difference between the length and width of each sensor stripe gives the stripe a shape asymmetry that produces a magnetic anisotropy along the lengthwise dimension. This anisotropy assists in maintaining the bias point (the magnetic moment under quiescent conditions) of the free layer when that bias point is also in the lengthwise direction as shown in FIG. 4a. However, the magnetic anisotropy cannot be too great or it will impede the variations in magnetic moment of the free layer under the action of external magnetic fields. Thus, some degree of additional magnetic anisotropy must be incorporated into the sensor stripe in order to produce the required sensor sensitivity. This will now be discussed with reference to FIG. 4b.

Referring to FIG. 4b there is shown a cross-sectional view of a single GMR stripe, such as either of the three stripes in FIG. 4a, illustrating, schematically, the preferred sequence of layers that form the GMR sensor stripe. Looking from the bottom up, there is shown a substrate (55), which can be a layer of oxide, a pinning layer (66), which can be a single layer of antiferromagnetic material, a pinned layer (77) which can be either a single layer of ferromagnetic material, such as CoFe or NiFe, formed to a thickness between approximately 10 and 100 angstroms or a laminated synthetic antiferromagnetic layer formed of two such ferromagnetic layers coupled by a non-magnetic coupling layer, a spacer layer (88) of a non-magnetic, electrically conducting material such as Cu, formed to a thickness between approximately 10 and 20 angstroms, a free layer (99) formed of a ferromagnetic material such as CoFe or NiFe, to a thickness between approximately 10 and 100 angstroms, and an overlayer (100) or capping layer to protect the sensor structure. The overlayer can be a portion of the surrounding insulating layers, which are formed of oxides or nitrides of Si or it can be a portion of the layer that supports the bonding sites for the magnetically tagged particles, the supporting layers being typically formed of similar insulating materials. After the sensor stripe is fabricated, the pinned and free layers are annealed to set their magnetic moment directions (i.e, their magnetizations) along the lengthwise dimension of the stripe as shown here as (777) and (999) also in FIG. 4a (as (11), (22) and (33)) so that the bias point (direction of the magnetic moment when the stripe is quiescent, i.e. is not acted on by external fields) is along the lengthwise direction of the stripe. It is further noted that the stripe is surrounded by layers of insulation (45), such as alumina or oxides or nitrides of silicon formed to thicknesses between approximately 1000 angstroms and 2 microns, to isolate it electrically from neighboring circuit elements (not shown) and that such insulating material will contribute to stresses exerted on the stripe.

By adjusting the spacer layer (88) the interlayer coupling between the free (99) and pinned (77) layers can be reduced so that the variation of the free layer magnetization in response to small external fields produces the required response of the sensor. Further, the free layer itself must be made as thin as possible, without sacrificing the dR/R of the sensor (the measure of its sensitivity), so that the free layer is responsive to small external fields. In addition, as is known in the art, the ferromagnetic layers exhibit the phenomenon of magnetostriction, which is typically defined in terms of a coefficient of magnetostriction. For example, NiFe alloy has a coefficient of magnetostriction that approaches zero at a composition of about 19% Fe. The coefficient becomes negative with less Fe and positive with more Fe. A thin layer (such as is formed herein) of positive coefficient of magnetostriction will exhibit a magnetic anisotropy in a direction of tensile stress on the layer. Likewise, a film having a negative coefficient of magnetostriction will exhibit a magnetic anisotropy in a direction of compressive stress on the layer. As the GMR sensor is a metallic stripe (as shown in FIG. 4b) encapsulated in surrounding insulation layers from above and below (and possibly including the substrate itself), it will generally be under anisotropic compressive or tensile stress that is substantially within the plane of the sensor layers. The magnitude of this stress will depend on the material forming the surrounding insulation layers and specific processes involved in their fabrication. The magnetostriction coefficient of the GMR sensor can be adjusted by its composition to give a magnetostriction coefficient that, when combined with the anisotropic stress of the surroundings, will result in a stress induced magnetic anisotropy that is perpendicular to the lengthwise direction of the stripe. For example, if the anisotropic stress of the GMR sensor is tensile in the lengthwise direction, the magnetically free layer magnetostriction coefficient is adjusted to be slightly negative, so that the stress induced magnetic anisotropy will be perpendicular to the lengthwise direction of the stripe while the magnitude is small enough so that the net anisotropy is still in the lengthwise direction.

Figure 5:
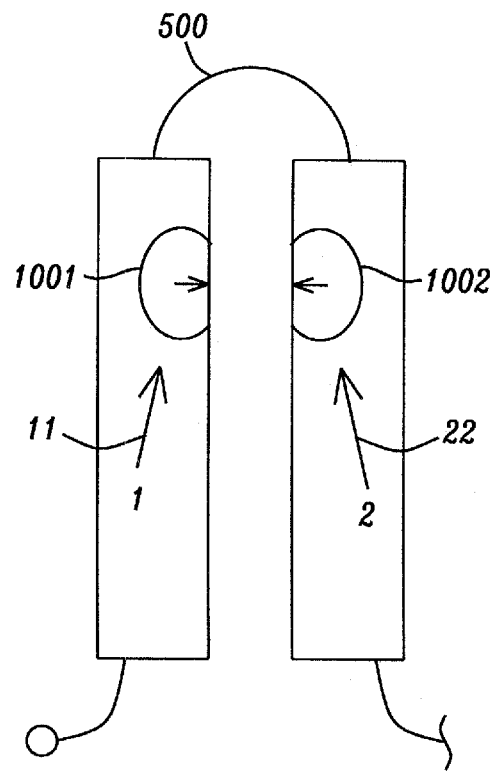
FIG. 5 is a schematic overhead view of two interconnected sensor stripes of the present invention showing the effects of a magnetized bead.

Referring now to FIG. 5, there is shown, schematically, just stripes 1 and 2 of the array in FIG. 4a. A magnetized bead (not shown) is located above the separation between the stripes and produces two lobes (1001) and (2002) defining equal-strength field lines of its magnetic field. The field vectors are directed as shown by the enclosed arrows, within the plane of the stripes. It can be seen that the parallel configuration of the adjacent stripes 1 and 2 and the new orientation of their magnetic moments (11) and (22) caused by the field of the magnetized bead, combined with the narrow separation between stripes, the narrowness of each stripe and the series connection of the stripes, produces a significant enhancement of the sensor's response. The maximum response of the sensor array to the presence of a magnetized particle occurs when the particle is over the separation between adjacent stripes, as shown in this figure. In that position, each of the two lobes causes a strong deflection of the magnetic moments of the respective stripes. Because of the series connection of the two stripes, the dR/R of each stripe effectively add to produce a doubling of the voltage drop across the array. If the magnetic bead is not precisely over the separation between stripes, the narrow width of each stripe still ensures that the magnetic field of the bead impinges on more than one stripe and enhances the response of the array.

As is finally understood by a person skilled in the art, the preferred embodiments of the present invention are illustrative of the present invention rather than limiting of the present invention. Revisions and modifications may be made to methods, materials, structures and dimensions employed in forming and providing a GMR sensor stripe array with a stable free layer bias point, while still forming and providing such an array and its method of formation in accord with the spirit and scope of the present invention as defined by the appended claims.

What is claimed is:

1. A sensor, comprising:
a substrate;
an integer plurality of M independent and substantially identical horizontally planar GMR sensor stripes formed on said substrate and horizontally disposed as separate elements on said substrate and electrically connected in a single, continuous series-only electrical circuit to form a linear, series connected serpentine horizontally disposed array of said separate, independent GMR sensor stripes, wherein said planar GMR sensor stripes are denoted successively 1 to M, each said planar GMR sensor stripe having a rectangular shape with a length dimension greater than a width dimension and wherein said width dimension is comparable to a diameter of small magnetic particles to be detected and wherein there is a sensitive magnetic bias direction along said length dimension resulting only from a combination of shape anisotropy and magnetostriction, and wherein the width dimension of each said planar GMR sensor stripe is bounded by a top widthwise edge and a bottom widthwise edge and wherein said length dimension is bounded by a left-side lengthwise edge and a right-side lengthwise edge and wherein said planar GMR sensor stripes are placed side by side and parallel to each other in a lengthwise direction in a common horizontal plane and aligned with their respective left-side and right-side lengthwise edges adjacent to each other, parallel to each other and separated from each other by a separation distance that is less than the diameter of a particle to be detected and wherein co-linear top widthwise edges of adjacent stripes denoted 1 and 2 are electrically connected by a conducting element and wherein co-linear bottom widthwise edges of adjacent stripes denoted 2 and 3 are electrically connected by a conducting element and wherein the remaining stripes from 3 to M are similarly connected so that the totality of stripes 1 to M form a linear serpentine array with a continuous electrically conducting pathway from a bottom widthwise edge of stripe 1 to a top widthwise edge of stripe M; whereby a common current entering at the bottom widthwise edge of stripe 1 and leaving from the top in said serpentine array runs in an opposite direction in any pair of adjacent stripes.

2. The sensor of claim 1 wherein, because said separation distance is less than a diameter of small magnetic particles to be detected by said sensor, a magnetic particle affixed above said adjacent stripes preferentially overlaps said adjacent stripes and simultaneously affects both said adjacent stripes in a manner that produces an addition of a resistance variation in each said stripe individually, thereby enhancing a detectability of said particle.

3. The sensor of claim 1 wherein said width dimension of each said stripe is approximately a diameter of a small magnetic particle to be detected.

4. The sensor of claim 1 further including an encapsulating surrounding layer of insulating material, said insulating material placing said stripes in a condition of anisotropic compressive or tensile stress which, together with said shape anisotropy, produces a stable yet sensitive magnetic biasing.

* * * * *